(12) United States Patent
Kempf et al.

(10) Patent No.: US 7,638,489 B2
(45) Date of Patent: Dec. 29, 2009

(54) **MODULATION OF ANGIOGENESIS BY *BARTONELLA HENSELAE***

(75) Inventors: Volkhard Kempf, Tubingen (DE); Tanja Riess, Tubingen (DE); Ingo Autenrieth, Tubingen (DE); Kari Alitalo, Helsinki (FI); Siv Anderson, Uppsala (SE)

(73) Assignee: Eberhard-Karls Universitat Tubingen Universitatsklinikum, Tubingen (DE)

( * ) Notice: Subject to any disclaimer, the term of this patent is extended or adjusted under 35 U.S.C. 154(b) by 286 days.

(21) Appl. No.: 11/429,657

(22) Filed: May 4, 2006

(65) Prior Publication Data

US 2006/0286122 A1 Dec. 21, 2006

Related U.S. Application Data

(63) Continuation of application No. PCT/EP2004/012273, filed on Oct. 29, 2004.

(30) Foreign Application Priority Data

Nov. 5, 2003 (DE) ............................... 103 51 627

(51) Int. Cl.
*A01N 37/18* (2006.01)
*A61K 39/00* (2006.01)
*A61K 39/38* (2006.01)
*A61K 39/02* (2006.01)
*A61K 38/00* (2006.01)
*A61K 38/16* (2006.01)

(52) U.S. Cl. ........................... 514/8; 514/2; 424/184.1; 424/190.1; 424/234.1

(58) Field of Classification Search ........................ None
See application file for complete search history.

(56) References Cited

U.S. PATENT DOCUMENTS 6,406,887 B1 6/2002 Anderson et al.
2006/0286122 A1* 12/2006 Kempf et al. ............ 424/200.1

FOREIGN PATENT DOCUMENTS

EP 1680499 A2 * 7/2006
WO WO 2005/049786 A2 * 6/2005

OTHER PUBLICATIONS

Dabo et al, Microbial Pathogenesis, 2006, 41:10-20.*
Hemsworth et al, European J. Oncology Nursing, 2006, 10:117-127.*
Kirby, Infection and Immunity, Dec. 2004, 72/12:7315-7317.*
Sood et al, Medical Hypotheses, 1997, 48:511-515.*
Wagner et al, International J. Medical Microbiology, 2008, 298:579-590.*
Dabo et al, Infection and Immunity, May 2006, 74/5:2513-2521.*
Kaiser et al, Cellular Microbiology, 2008, pp. 1-12.*
Dehio, Current Opinion in Microbiology, 1999, 2:78-82.*
Kempf et al, Trends in Microbiology, Jun. 2002, 10/6:269-275.*
Riess et al, Infection and Immunity, Jan. 2007, 75/1:35-43.*
Szczesny et al, PLoS Pathogens, Aug. 2008, 4/8:1-12.*
Lazar et al, Mol. and Cell. Biol., 1988, 8:1247-1252.*
Burgess et al, JCB, 1990, 111:2129-2138.*
Kumar et al, PNAS, 1990, 87:1337-1341.*
Creighton, In: Proteins, Structures and Molecular Prinicples, 1984, pp. 314-315.*
Creighton, In: Protein Structure a practical approach, 1990, pp. 184-186.*
Nosoh et al, In: Protein Stability and Stabilization Through Protein Engineering, 1991, pp. 198-217.*
Bowie et al, Science, 1990, 247/4948:1306-1310.*
Chomel et al, Vet. Res., 2009, 40:29, 22 pages.*
Greub et al, J. Med. Microbiol., 2002, 51:915-923.*
Alsmark, C. (2004) "The louse-borne human pathogen *Bartonella quintana* is a genomic derivative of the zoonotic agent *Bartonella henselae*" PNAS 101:9716-9721.
Blum, W. et al. (1990) "A specific radioimmunoassay for the growth hormone (gh)-dependent somatomedin-binding protein: its use for diagnosis of gh deficiency" Journal of Clinical Endocrinology and Metabolism 70:1292-1298.
Burgess, A. et al. (1998) "Outer membrane proteins of *Bartonella henselae* and their interaction with human endothelial cells" Microbial Pathogenesis 25:157-164.
Ikeda, E. et al. (1995) "Hypoxia-induced transcriptional activation and increased mrna stability of vascular endothelial growth factor in c6 glioma cells" The Journal of Biological Chemistry 270:19761-19766.
Kempf, V. et al. (2001) "Evidence of a leading role for vegf in *Bartonella henselae*-induced endothelial cell proliferations" Cellular Microbiology 3:623-632.
Kibbe, (2000) "Handbook of pharmaceutical Excipients" American Pharmaceutical Association and Pharmaceutical Press, 3$^{rd}$ edition, Textbook.
Raleigh, J. (1998) "Hypoxia and vascular endothelial growth factor expression in human squamous cell carcinomas using pimonidazole as a hypoxia marker" Cancer Research 58:3765-3768.
Regnery, R. et al. (1992) "Characterization of a novel *Rochalimaea* species, r. *henselae* sp. Nov., isolated from blood of a febrile, human immunodeficiency virus-positive patient" Journal of Clinical Microbiology 30:265-274.

(Continued)

*Primary Examiner*—N. M Minnifield
(74) *Attorney, Agent, or Firm*—Knobbe Martens Olson & Bear LLP

(57) ABSTRACT

The present invention relates to *Bartonella henselae* as a component of a pharmaceutical composition for the modulation of the angiogenesis; a nucleic acid molecule that is derived from the gene encoding the *Bartonella henselae* adhesin A protein (BadA), a vector comprising said nucleic acid molecule; a host containing said nucleic acid molecule or said vector; a (poly)peptide encoded by said nucleic acid molecule; a composition comprising *Bartonella henselae* bacteria; a composition comprising aforesaid (poly)peptide; a method for treating a human or animal being in need of the modulation of the angiogenesis, a method for detecting an infection by *Bartonella* in a human or animal being, as well as a method for immunizing a cat.

5 Claims, 12 Drawing Sheets

OTHER PUBLICATIONS

Resto-Ruiz, S. et al. (2002) "Induction of a potential paracrine angiogenic loop between human thp-1 macrophages and human microascular endothelial cells during *Bartonella henselae* infection" Infection and Immunity 70:4564-4570.

Riess, T. et al. (2003) "Rapid and efficient trasposon mutagenesis of *Bartonella henselae* by trasposome technology" Gene 313:103-109.

Riess, T. et al. (2004) "*Bartonella* adhesion a mediates a proangiogenic host cell response" J. Exp. Med. 200:1267-1278.

Sambrook, J. et al. (2001) "Molecular cloning—a laboratory manual" Cold Spring Harbor Laboratory Press, New York, $3^{rd}$ Edition, Textbook.

Schulte, R. et al. (2000) "*Yersinia enterocolitica* invasion protein triggers il-8 production in epithelial cells via activation of rel p65-p65 homodimers" The FASEB Journal 14:1471-1484.

* cited by examiner

SEQ ID No. 1

```
ATGTTTTGGATGTGCTTTGTAATTTTTTTCATTGGAGAATTTATTATGAAAAAATTATCTGTCAC
ATCAAAGAGACAATATAATTTATATGCTTCGCCTATTTCTCGACGTTTATCTTTGTTAATGAAGC
TCTCATTGGAAACTGTAACAGTTATGTTCTTATTGGGTGCATCTCCTGTATTGGCTTCGAATCTT
GCGCTTACAGGAGCAAAGAATCTGAGTCAAAACTCTCCAGGTGTAAATTACTCTAAAGGTAGCCA
TGGTAGTATTGTTCTCTCTGGTGATGATGATTTTGCGGTGCGGATTATGTTCTTGGTCGTGGAG
GCAATTCTACTGTACGTAATGGATTCCAATAAGTGTAGAAGAAGAATATGAGAGATTTGTCAAA
CAAAAATTAATGAATAATGCTACTTCTCCTTATAGTCAGAGTTCAGAGCAACAAGTTTGGACTGG
TGATGGGCTAACAAGCAAAGGTTCGGGTTATATGGGAGGGAAGTCGACTGACGGTGATAAAAATA
TCTTGCCTGAGGCTTATGGTATATATTCTTTTGCAACTGGTTGTGGTTCTTCTGCGCAGGGGAAT
TATTCAGTTGCATTTGGTGCAAATGCAACTGCACTTACTGGGGGGTCGCAAGCTTTTGGTGTTGC
TGCACTTGCAAGTGGAAGGGTAAGTGTTGCTATTGGTGTAGGGTCAGAAGCGACGGGAGAGGCTG
GAGTTTCTTTGGGTGGACTCTCAAAGGCAGCTGGTGCTCGTAGTGTTGCTATAGGGACGCGGGCC
AACGCTTACGGTGAAGAATCTATTGCGATAGGTGGTGGCTTAAAACAGGGCAGTGATAATAAGAT
CGGTTCAGCTGTAGCGCAGGGTCTGAAAGCGATTTCTATAGGTTCTGATTCTGTTGGTTTTCAGC
ACTATGCAGTTGCTATTGGTGCTAAATCCCGTGCTCTTCTCTTGAAAAGTGTTGCCTTGGGTTCT
TATTCTGTTGCTGATGTTGATGCTGGCGTTAGAGGTTATGATCCTGTGGAGGATGAGCCATCGAA
AAACGTTAGTTTTGTATGGAAAAGCTCTGTAGGTGCTGTTAGTGTTGGTAATCGTAAAGAAGGCT
TAACGCGACAAATTATAGGAGTTGCAGCTGGTACTGAAGACACTGATGCAGTAAATGTTGCACAG
CTAAAAGCATTAAGGGGAATGATATCAGAAAAAGGAGGTTGGAATCTTACTGTTAATAATGACAA
TAATACAGTTGTTAGTTCAGGTGGTGCATTAGATTTGTCATCTGGAAGTAAAAATCTCAAAATTG
CAAAAGATGGAAAAAGAATAATGTAACCTTTGATGTCGCTAGGGATCTCACGTTAAAGAGCATA
AAATTAGACGGTGTTACTTTAAATGAAACAGGTTTATTTATTGCAAACGGACCACAAATCACCGC
TTCAGGTATTAATGCTGGTAGTCAAAAAATTACAGGCGTAGCAGAGGGTACTGATGCGAACGATG
CAGTAAACTTTGGACAACTGAAGAAAATTGAAACAGAAGTCAAAGAACAAGTAGCAGCCAGTGGC
TTTGTGAAACAGGATAGCGATACAAAATACCTTACCATTGGTAAGGATACAGATGGCGATACAAT
CAATATTGCTAATAACAAAAGTGATAAGCGTACTCTCATGGGCATAAAGGAGGGTGACATCTCAA
AAGACTCGAGTGAAGCTATCACCGGTTCACAGCTATTTACTACAAATCAAAATGTGAAAACTGTA
TCAGATAATCTCCAAACAGCAGCCACGAATATAGCTAAGACTTTTGGAGGTGATGCCAAATATGA
AGATGGTGAATGGACTGCTCCGACATTTAAAGTTAAAACTGTTACCGGTGAAGGCAAGGAAGAAG
AGAAGACGTATCAGAATGTAGCGGATGCCTTGGCTGGAGTTGGAAGTTCCATCACCAATGTTCAG
AATAAAGTGACTGAACAAGTTAATAATGCGATTACTAAAGTGGAAGGCGATGCCTTATTATGGAG
CGATGAAGCTAATGCCTTTGTGGCGCGTCATGAAAGAGTAAGTTAGAAAAAGGCGCATCTAAAG
CGACACAAGAAAACAGCAAGATTACGTATCTGTTAGATGGTGATGTTTCGAAAGATTCCACGGAT
GCTATTACAGGTAAACAGCTTTATTCATTAGGTGATAAGATTGCATCTTATTTAGGTGGTAACGC
```

Fig. 7A

```
TAAATATGAGAATGGTGAATGGACTGCACCTACCTTTAAGGTTAAAACAGTTAAGGAAGATGGTA
AGGAAGAAGAGCAGACGTATCATAATGTAGCAGCGGCTTTTGAAGGAGTTGGTACGTCTTTCACG
AATGTGAAAAATGAAATTACTAAACAGATTAATCATCTCCAGTCTGATGATTCAGCGGTTGTTCA
TTATGATAAAGATGATAAAAACGGCAGTATTAATTATGCGAGTGTAACCTTGGGTAAAGGTAAAG
ATTCTGCAGCTGTTACCCTTCATAATGTCGCTGCAGGTAATATTGCTAAGGATTCACATGATGCA
ATCAATGGTAGCCAAATTTATTCTCTGAACGAGCAACTTGCGACCTATTTTGGTGGCGGTGCTGG
TTATAATAAGGAAGGCAAATGGACTGCTCCAACTTTTACAGTCAAGACAGTTAAGGAAGATGGTG
AGGAAGAAGAGAAGACGTATCAGAATGTAGCGGAAGCTTTGACTGGAGTTGGTACGTCTTTCACC
AATATAAAAGTGAGATTACTAAACAGATTGCTAATGAGATTAGCAATGTAACAGGTGATAGTCT
TGTTAAGAAAGATCTCGATACGAATCTTATCACCATTGGTAAAGAAGTAGCAGGTACTGAAATCA
ATATAGCAAGCGTTTCTAAAGCTGACCGGACTCTTTCTGGTGTTAAGGAAGCAGTAAAAGATAAT
GAAGCTGTTAACAAAGGGCAGCTTGATAAAGGTTTGAAGCATCTTTCTGACAGTCTCCAGTCCGA
AGATTCAGCAGTTGTTCATTATGATAAAAAGACAGATGAAACTGGTGGCATTAATTATACGAGCG
TGACGTTGGGAGGTAAAGATAAGACCCCTGTTGCCCTTCATAATGTCGCTGATGGTAGTATTTCC
AAGGATTCACATGATGCCATCAATGGCGGACAGATTCATACAATCGGTGAGGATGTTGCAAAATT
CTTGGGTGGAGCAGCAAGCTTTAACAACGGTGCTTTTACCGGCCCAACTTATAAGTTGTCGAATA
TTGATGCAAAGGGTGATGTACAACAGAGTGAGTTTAAAGATATAGGTTCAGCCTTTGCGGGTCTT
GATACGAACATCAAGAATGTCAATAATAATGTAACGAATAAGTTTAATGAACTTACTCAAAACAT
AACGAATGTTACGCAACAGGTAAAAGGCGATGCCTTATTATGGAGCGATGAAGCCAATGCCTTTG
TGGCGCGTCATGAAAAGAGCAAGTTAGGAAAAGGTGCATCTAAAGCGACACAAGAAAACAGCAAG
ATTACGTATCTGTTAGATGGTGATGTTTCGAAAGATTCCACGGATGCTATTACAGGTAAACAGCT
TTATTCATTAGGTGATAAGATTGCATCTTATTTAGGTGGTAACGCTAAATATGAGGATGGTGAAT
GGACTGCACCTACCTTTAAGGTTAAAACAGTTAAGGAAGATGGTAAGGAAGAAGAGAAGACTTAT
CAGAATGTAGCGGAAGCTTTGACTGGAGTTGGTACGTCTTTCACGAATGTGAAAAATGAAATTAC
TAAACAGATTAATCATCTCCAGTCTGATGATTCAGCGGTTGTTCATTATGATAAGAATAAAGATG
AAACTGGTGGCATTAATTATGCGAGTGTAACCTTGGGTAAAGGTAAAGATTCTGCAGCTGTTACC
CTTCATAATGTTGCTGATGGTAGTATTTCCAAGGATTCACGTGATGCCATCAATGGTAGCCAAAT
TTATTCTCTGAACGAGCAACTTGCGACCTATTTTGGCGGCGGTGCTAAGTACGAGAATGGCCAAT
GGACCGCTCCTATTTTTAAAGTCAAGACAGTTAAGGAAGATGGTGAGGAAGAAGAGAAGACGTAT
CAGAATGTAGCGGAAGCTTTGACTGGAGTTGGTACGTCTTTCACAAATATAAAGAGTGAGATTAC
TAAACAGATTGCTAATGAGATTAGCAGTGTAACAGGTGATAGTCTTGTTAAGAAAGATCTCGCCA
CGAATCTTATCACCATTGGTAAAGAAGTAGCAGGTACTGAAATCAATATAGCAAGCGTTTCTAAA
GCTGACCGGACTCTTTCTGGTGTTAAGGAAGCAGTAAAAGATAATGAAGCTGTTAACAAAGGGCA
GCTTGATACCAATATCAAGAAAGTAGAAGATAAATTAACAGAAGCAGTCGGTAAAGTTACGCAAC
AGGTGAAAGGTGATGCTTTATTGTGGAGCAATGAAGATAACGCGTTTGTTGCTGATCATGGTAAG
GATAGTGCAAAGACAAAGAGCAAGATTACACATTTATTAGATGGAAATATTGCGTCTGGCTCAAC
```

Fig. 7B

```
CGATGCCGTTACCGGTGGTCAACTCTATTCTCTGAACGAGCAACTTGCGACCTATTTTGGCGGCG
GTGCTAAGTACGAGAATGGCCAATGGACTGCACCTACCTTTAAGGTTAAAACAGTTAACGGTGAA
GGCAAGGAAGAAGAGCAGACTTATCAGAATGTAGCGGAAGCTTTGACTGGAGTTGGTGCGTCTTT
CATGAATGTTCAGAATAAAATTACTAATGAAATTACCAATCAAGTTAATAACGCAATTACGAAAG
TAGAAGGCGATAGTCTTGTGAAGCAAGATAATCTTGGTATTATTACGCTTGGTAAAGAAAGAGGT
GGTTTGAAAGTTGATTTTGCAAATCGTGATGGTTTAGATCGGACTCTTTCTGGTGTAAAGGAAGC
GGTAAACGATAATGAAGCAGTTAATAAAGGCCAGCTTGATGCCGATATCAGTAAAGTTAATAATA
ATGTAACGAATAAGTTTAATGAACTTACTCAAAACATAACGAATGTTACGCAACAGGTAAAAGGC
GATGCCTTATTATGGAGCGATGAAGCTAATGCCTTTGTGGCGCGTCATGAAAGAGTAAGTTAGA
AAAAGGCGTATCTAAAGCGACACAAGAAAATAGCAAGATTACGTATCTGTTAGATGGTGATATTT
CGAAAGGTTCCACGGATGCCGTTACCGGTGGTCAGCTTTATTCTCTGAACGAGCAACTTGCGACC
TATTTTGGTGGCGATGCTAAGTACGAGAATGGCCAATGGACTGCACCTACCTTTAAGGTTAAAAC
AGTTAACGGTGAAGGCAAGGAAGAAGAGCAGACGTATCATAATGTAGCAGCAGCTTTTGAAGGAG
TTGGTACGTCTTTCACCAATATAAAAAGTGAGATTACTAAACAGATTAATAATGAGATTAGCAAT
GTAAAAGGTGATAGTCTTGTTAAGAAAGATCTCGCCACGAATCTTATCACCATTGGTAAAGAAGT
AGCGGGTACTGAAATCAATATAGCAAGCGTTTCTAAAGCTGACCGGACTCTTTCTGGTGTAAAGG
AAGCAGTAAAAGATAATGAAGCTGTTAACAAAGGGCAGCTTGATACCAATATCAAGAAAGTAGAA
GATAAATTAACAGAAGCAGTCGGTAAAGTTACGCAACAGGTAAAAGGTGATGCTTTATTGTGGAG
CAATGAAGATAACGCGTTTGTTGCTGATCATGGTAAGGATAGCGCAAAGACAAAGAGCAAGATTA
CACATTTATTAGATGGAAATATTGCGTCTGGCTCAACCGATGCCGTTACCGGTGGTCAGCTTTAT
TCTCTGAACGAGCAACTTGCGACCTATTTTGGCGGCGGTGCTAAGTACGAGAATGGCCAATGGAC
TGCACCTACCTTTAAGGTTAAAACAGTTAACGGAGATGGCAAGGAAGAAGAGCAGACTTATCAGA
ATGTAGCGGAAGCTTTGACTGGAGTTGGTACGTCTTTCACGAATGTTCAGAATAAAATTACTAAT
GAAATTACCAATCAAGTTAATAACGCAATTACGAAAGTAGAAGGCGATAGTCTTGTGAAGCAAGA
TAATCTTGGTATTATTACGCTTGGTAAAGAAGAGGTGGTTTGAAAGTTGATTTTGCAAATCGTG
ATGGTTTAGATCGGACTCTTTCTGGTGTAAAGGAAGCGGTAAACGATAATGAAGCAGTTAATAAA
GGCCAGCTTGATGCCAATATCAGTAAAGTTAATAATAATGTAACGAATAAGTTTAATGAACTTAC
TCAAAACATAACGAATGTTACACAACAAGTTCAAGGTGATACTTTATTATGGAGCGATGAAGCTA
ATGCCTTTGTGGCGCGTCATGAAAGAGTAAGTTAGAAAAAGGCGTATCTAAAGCGACACAAGAA
AATAGCAAGATTACGTATCTGTTAGATGGTGATATTTCGAAAGGTTCCACGGATGCCGTTACCGG
TGGTCAGCTTTATTCTCTGAACGAGCAACTTGCGACCTATTTTGGCGGCGGTGCTAAGTACGAGA
ATGGTGAATGGACCGCACCTACCTTTAAGGTTAAAACAGTTAACGGTGAAGGCAAGGAAGAAGAG
CAGACGTATCATAATGTAGCAGCAGCTTTTGAAGGAGTTGGTACGTCTTTCACCAATATAAAAAG
TGAGATTACTAAACAGATTGATAATGAGATTATCAATGTAAAAGGTGATAGTCTTGTTAAGAGAG
ATCTCGCTACGAATCTCATCACCATTGGTAAAGAAATAGAAGGCAGTGCAATCAATATTGCTAAT
AAGAGTGGTGAAGCTCGGACCATTTCTGGTGTAAAGGAAGCAGTAAACAATAATGAAGCTGTTAA
```

Fig. 7C

```
CAAAGGGCAACTTGATACCAATATCAAGAAAGTAGAAGATAAATTAACAGAAGCAGTCGGTAAAG
TTACGCAACAGGTAAAAGGTGATGCTTTATTGTGGAGCAATGAAGATAACGCGTTTGTTGCTGAT
CATGGTAAGGATAGCGCAAAGACAAAGAGTAAGATTACACATTTATTAGATGGAAATATTGCGTC
TGGCTCAACCGATGCCGTTACCGGTGGTCAACTCTATTCTCTTAACGAGCAACTTGCGACCTATT
TTGGCGGCGGTGCTAAGTACGAGAATGGCCAATGGACTGCACCTAGCTTTAAGGTTAAAACAGTT
AAGGAAGATGGCAAGGAAGAAGAGCAGACGTATCAGAATGTAGCGGAAGCTTTGACTGGAGTTGG
TACGTCTTTCACGAATGTGAAAAATGAAATTACTAAACAGATTAATCATCTCCAGTCTGATGATT
CAGCGGTTGTTCATTATGATAAGAATAAAGATGAAACTGGTACCATTAATTATGCGAGTGTAACC
TTGGGTAAAGGTAAAGATTCTGCAGCTGTTACCCTTCATAATGTCGCCGATGGTAGTATTTCCAA
GGATTCACGTGATGCCATCAATGGTGGACAGATTCATACAATCGGTGAGGATGTTGCAAAATTCT
TGGGTGGAGATGCAGCTTTTAAAGATGGTGCTTTTACCGGCCCAACTTATAAGTTGTCGAATATT
GATGCAAAGGGTGATGTACAACAGAGTGAGTTTAAAGATATAGGTTCAGCCTTTGCGGGTCTTGA
TACGAACATCAAGAATGTCAATAATAATGTAACGAATAAGTTTAATGAACTTACTCAAAGCATAA
CGAATGTTACGCAACAGGTAAAAGGCGATTCCTTATTATGGAGCGATGAAGCCAATGCCTTTGTG
GCGCGTCATGAAAAGAGCAAGTTAGAAAAGGTGCATCTAAAGCGATACAAGAAAATAGCAAGAT
TACGTATCTGTTAGATGGTAATGTTTCGAAAGGTTCCACGGATGCCGTTACTGGTGGTCAGCTTT
ATTCAATGAGCAACATGCTTGCGACCTATTTAGGTGGTAACGCTAAATATGAGAATGGTGAATGG
ACCGCACCTACCTTTAAGGTTAAAACAGTTAACGGTGAAGGCAAGGAAGAAGAGCAAACTTATCA
GAATGTAGCGGAAGCTTTGACTGGAGTTGGTACGTCTTTCACCAATATAAAAAGTGAGATTGCCA
AACAGATTAATCATCTCCAGTCTGATGATTCAGCGGTTATTCATTATGATAAGAATAAAGATGAA
ACTGGCACCATTAATTATGCGAGTGTAACTTTGGGTAAAGGTGAAGATTCTGCAGCTGTTGCCCT
TCATAATGTCGCTGCAGGTAATATTGCTAAGGATTCACGTGATGCAATCAATGGTTCTCAGCTTT
ATTCTTTGAACGAGCAGTTATTGACCTATTTTGGCGGTAATGCTGGCTATAAAGATGGGCAATGG
ATAGCTCCCAAATTCCAAGTTTCGCAGTTCAAGAGTGATGGTAGTTCTGGTGAGAAGGAGAGCTA
TGATAATGTAGCGGCTGCGTTTGAAGGAGTTAACAAAAGTCTTGCAGGTATGAACGAGCGTATTA
ATAATGTTGTTACTGCTGGCCAGAATGTTTCGTCGAACAGTTTAAATTGGAATGAGACAGAGGGA
GGTTATGACGCTCGTCATAATGGTGTGGACAGTAAGCTCACGCATGTAGAGAATGGTGACGTATC
CGAAAAATCGAAAGAAGCCGTTAATGGAAGTCAACTATGGAATACGAATGAGAAAGTTGAAGCGG
TTGAGAAGGATGTAAAGAATATTGAGAAGAAGGTACAAGATATTGCTACAGTAGCAGATAGTGCT
GTTAAGTATGAGAAAGATAGTACTGGCAAGAAAACGAATGTAATCAAATTAGTTGGTGGGAGTGA
AAGTGATCCAGTATTGATAGACAATGTAGCGGATGGTGACATTAAAGAAGGCTCTAAGCAGGCAG
TCAATGGAGGTCAGTTGCGTGATTATACTGAGAAACAGATGAAGATAGTGCTTGAAGATGCGAAG
AAATATACGGATGAACGCTTCAATGATGTCGTCAATAATGGTGTTAATGAGGCTAAAGCTTATAC
AGATATGAAGTTTGAGGCTTTAAGTTACGCTGTTGAGGATGTCCGTAAAGAAGCAAGACAGGCGC
AGCTATTGGTTTGGCGGTATCTAACTTACGTTACTATGATATACCGGGATCTTTAA
```

Fig. 7D

MODULATION OF ANGIOGENESIS BY *BARTONELLA HENSELAE*

CROSS REFERENCE TO RELATED APPLICATIONS

This application is a continuation of copending International Patent Application PCT/EP/2004/012273 filed on Oct. 29, 2004 and designating the United States, which claims priority of German Patent Application DE 103 51 627.1 filed on Nov. 5, 2003, which is incorporated herein by reference.

BACKGROUND OF THE INVENTION

1. Field of the Invention

The present invention relates to *Bartonella henselae* as a component of a pharmaceutical composition for the modulation of the angiogenesis; a nucleic acid molecule that is derived from the gene encoding the *Bartonella henselae* adhesin A protein (BadA), a vector comprising said nucleic acid molecule; a host containing said nucleic acid molecule or said vector; a (poly)peptide encoded by said nucleic acid molecule; a composition comprising *Bartonella henselae* bacteria; a composition comprising aforesaid (poly)peptide; a method for treating a human or animal being in need of the modulation of the angiogenesis, a method for detecting an infection by *Bartonella* in a human or animal being, as well as a method for immunizing a cat.

2. Related Prior Art

Angiogenesis or neovascularisation refers to a process in which under physiological conditions new blood vessels are sprouting out of the existing vascular system. Angiogenesis can, e.g., be observed during embryogenesis in the corpus luteum (menstruation). Furthermore, angiogenesis has a pathophysiological relevance, it can be observed during the wound healing, in diabetic retinopathy, haemangiomas, psoriasis, as well as in malignant tumors. In this connection, ischaemic diseases are especially relevant, which are very often characterized by a disorder of the angiogenesis.

Against this background especially in medicine and pharmacology there is a considerable need for pharmacological effective substances by which the angiogenesis can be modulated.

SUMMARY OF THE INVENTION

Therefore, the object of the present invention is to provide a substance for modulating the angiogenesis. Furthermore, such a substance should be provided that can easily and cost-effectively be obtained or prepared.

According to the invention this object is achieved by the usage of *Bartonella henselae* as a compound of a pharmaceutical composition for the modulation of the angiogenesis.

This object can also be realized by the following method, comprising the steps: (a) providing *Bartonella henselae* and (b) formulating *Bartonella henselae* into a pharmaceutically acceptable carrier.

The inventors could surprisingly demonstrate that incubating biological replicating material, such as HeLa cells, with *Bartonella henselae* results in an a manipulation of the genetic program of said biological material, that is responsible for the regulation of the angiogenesis. In other words, the inventors have succeeded in demonstrating that *Bartonella henselae* is a substance that is suitable for the targeted modulation of the angiogenesis.

The finding that a gram-negative bacterium of the genus *Bartonella*, namely *Bartonella henselae*, enables the modulation of the angiogenesis and has therewith a therapeutical capacity was especially surprising, since this bacterium is largely described in the art as a trigger for the induction of a number of different diseases: *Bartonella henselae* was detected in the blood of immunosuppressed patients, for example HIV patients. Such patients which were infected by *Bartonella henselae*, show symptoms of the bacillary angiomatosis, bacillary peliosis (infestation of viscera), fever, bacteraemia and endocarditis. In immunocompetent hosts *Bartonella henselae* is the main pathogen that causes the so-called cat scratch disease (CSD).

It is also known that *Bartonella henselae* stimulates the production of growth factors or cytokines, for example of vascular endothelial growth factor (VEGF; cf. for this Kempf et al. (2001), "Evidence of a leading role for VEGF in *Bartonella henselae*-induced endothelial cell proliferations", *Cell. Microbiol.* 3(9), 623-632; Resto-Ruiz et al. (2002), "Induction of a potentional paracrine angiogenetic loop between human THP-1 macrophages and human microvascular endothelial cells during *Bartonella henselae* infection", *Infection and Immunity* 70(8), 4564-4570.

However, there are no hints in the art, which demonstrate or even suggest a relation between *Bartonella henselae* and the modulation of the angiogenesis.

Within the scope of the invention modulation of the angiogenesis refers to every largely targeted manipulation of the angiogenesis in a human or animal organism or parts or organs thereof, respectively, by *Bartonella henselae* or by parts of this bacterium, such as the stimulation, induction or inhibition of the angiogenesis.

It is preferred if the entire bacterium is used for the modulation of the angiogenesis.

This means that according to this embodiment the angiogenesis-modulating activity is based on the whole bacterium, the latter, therefore, can be used as such as an effective agent without any further processing measures, for example by performing a targeted infection. This measure has the advantage that the whole bacterium is available in large amounts and can be cultivated and reproduced by means of well-established microbiological methods.

According to a preferred embodiment of the invention, for modulating the angiogenesis a genetically modified bacterium is used.

A genetically modified bacterium refers to such a *Bartonella henselae* bacterium that differs in its pheno- or genotype in some way from that of the corresponding wild type bacterium. This measure has the advantage, that on the one hand the angiogenesis-modulating activity of the bacterium can be altered by means of molecular biological methods in a targeted fashion, and on the other hand possible pathogenic factors can be simultaneously knocked-out in a targeted fashion. Methods for the genetic modification of the bacterium are well-known in the art; cf. for example Sambrook, J. and Russell, D. W. (2001), "Molecular Cloning—A Laboratory Manual", Cold Spring Harbor Laboratory Press, New York, 3rd Edition.

According to the invention it is also preferred, if a killed bacterium is used for the modulation of the angiogenesis.

According to the invention a killed bacterium refers to such a bacterium that has lost its dividing activity and/or metabolic activity, however, such a bacterium is still able to modulate the angiogenesis. This measure has the advantage that such a *Bartonella henselae* bacterium is still in the position for presenting angiogenesis-modulating activity in biological material, as this was found by the inventors, however, it does not evolve any pathogenic activity.

According to a variation of the invention, for modulating the angiogenesis a peptide is used, that comprises a fragment of the adhesin A protein of *Bartonella henselae* (BadA).

This variation is also realized by the following method, comprising the steps: (a) Providing BadA and (b) formulating BadA into a pharmaceutically acceptable carrier. I.e., the *Bartonella henselae* bacterium is reduced to its BadA protein.

The inventors were able to identify a new protein referred to as *Bartonella henselae* adhesin A (BadA) as a crucial bacterial factor that is involved in the modulation of the angiogenesis. BadA is a bacterial protein having a molecular weight of 340 kD, and is encoded by a gene having the length of 9.3 kB. The DNA sequence of the BadA gene is presented in the attached sequence listing and referred to as SEQ ID No. 1. This protein is expressed at the bacterial surface of *Bartonella henselae*, and is visible in the electron microscope due to its enormous size.

As the inventors have realized, within the scope of the present invention and according to this preferred embodiment, for modulating the angiogenesis a peptide fragment can be used that is characteristic for BadA, i.e. such a fragment that displays the biological activity of BadA, which is responsible for the modulation of the angiogenesis, as, e.g., a segment of the whole protein, that is responsible for the adhesion of the bacterium to the host cells or the endothelial tissue of the host. Segments of the BadA protein which do not contribute to the angiogenesis-modulating activity, such as protein domains which merely serve for anchoring the protein in the membrane can be neglected. It goes without saying, that within the scope of the invention for modulating the angiogenesis also the whole BadA protein can be used, as well as fusion proteins which comprise a corresponding fragment of BadA displaying angiogenesis-modulating activity. With the present invention also the usage of such peptides is encompassed, which comprise a fragment of BadA that is modified compared to the wild type BadA, for example due to modified or substituted amino acids, as long as by this measure the angiogenesis-modulating activity of BadA is not lost.

On account of the therapeutical relevance of the findings of the inventors, it is preferred according to the invention if the modulation of the angiogenesis in the afore-mentioned usages occurs within the frame of the treatment of an ischaemic disease.

Especially in ischaemic diseases, i.e. such diseases characterized by a decreased or interrupted blood circulation through an organ, a part of an organ or a tissue resulting from disordered arterial blood supply, a targeted modulation of the angiogenesis is envisaged in order to normalize the circulation, that is so far not possible in the art or merely in an unsatisfactory way. Here, the present invention gives remedy by activating or upregulating genetic factors, such as growth factors or cytokines, resulting in the induction of the angiogenesis in an affected patient.

This measure has the advantage that herewith especially ischaemic conditions are redressed or reduced, and aid can be given to affected patients in a targeted manner. The inventors were able to show that *Bartonella henselae* or BadA have a special angiogenesis-stimulating potential that results from an up-regulation of different genes inducing the angiogenesis in biological material, if said biological material is incubated together with *Bartonella henselae* or BadA for a certain time, or if cells are infected by *Bartonella henselae*.

Very often especially in tumor diseases the angiogenesis should be manipulated in a targeted fashion in order to, e.g., modulate or inhibit the blood flow in tumors. Therefore, it is preferred according to the invention, if in the afore-explained usages the modulation of the angiogenesis occurs within the frame of the treatment of a tumor disease. Of course, while doing so further anti-carcinogenic measures can be performed, such as a chemotherapy.

In this connection on account of the present invention it is possible to analyze substances which are not known so far in view of their capacity to modulate the angiogenesis by screening these substances in an in vitro assay system. In such an assay system it can be studied whether such substances are competitive with *Bartonella henselae* or BadA, e.g. whether they have a similar, i.e. angiogenesis-stimulating activity, or whether they have an activity that is contradictory to that of *Bartonella henselae* or BadA, and, therefore, inhibit the angiogenesis.

Another subject of the present invention relates to a nucleic acid molecule encoding a (poly)peptide that is associated with the modulation of the angiogenesis, said nucleic acid molecule comprises a segment having the sequence SEQ ID No. 1.

The sequence SEQ ID No. 1 that is shown in FIG. 7, is the sequence of the gene encoding the bacterial adhesin A protein of *Bartonella henselae* (BadA) and has a size of 9.3 kB. According to the invention, the afore-described nucleic acid molecule also encompasses such a molecule that encodes the whole BadA protein but also such a molecule that encodes protein segments which display BadA activity, i.e. angiogenesis-modulating activity. Furthermore, according to the invention also such nucleic acid molecules are meant, which encode (poly)peptides derived from BadA and in which, e.g., different amino acids were replaced or chemically modified, as long as this (poly)peptide still displays BadA activity, i.e. angiogenesis-modulating activity. Furthermore, according to the invention this object also encompasses such a nucleic acid molecule that comprises at its 5'- and/or 3'-ends additional sequences which are independent from SEQ ID No. 1 and which, e.g., serve for the expression, replication, purification, etc. of the genetic information or the (poly)peptide, respectively.

Another object of the present invention is a vector that comprises the before-described nucleic acid molecule, i.e. a corresponding genetically modified element, such as a plasmid, virus, bacteriophage or a cosmid, that can be used for transferring and/or inserting the nucleic acid molecule into a host cell. A further object of the invention is a host, such as a bacterium, a cell or an organism, into which the before-described nucleic acid molecule or the vector comprising this nucleic acid molecule was introduced. Besides, the present invention relates to a (poly)peptide that is encoded by the before-described nucleic acid molecule.

Against this background the present invention also relates to a composition that comprises *Bartonella henselae* bacteria or the before-explained (poly)peptide that is derived from the *Bartonella henselae* adhesin A protein (BadA) or that corresponds to BadA.

In this composition the bacteria can either be present alive or deadened. Moreover, also genetically modified bacteria can be used in this connection. By means of both measures pathogenic factors can be eliminated, whereas the angiogenesis-modulating activity is conserved or is even enhanced.

These compositions are preferably pharmaceutical compositions for the modulation of the angiogenesis and comprise a pharmaceutically acceptable carrier as well as, if appropriate, further auxiliary agents. Such pharmaceutical auxiliary agents are well-known in the art; cf. for example A. Kibbe, "Handbook of Pharmaceutical Excipients", American Pharmaceutical Association and Pharmaceutical Press, 3rd edition (2000).

Another object of the present invention is a method for detecting a Bartonella infection in a human or animal being, comprising the following steps: (a) providing a biological sample of a living being; (b) analyzing the biological sample for the existence of antibodies against the Bartonella henselae adhesin A protein (BadA), and (c) correlating a positive finding in step (b) with an infection by Bartonella.

Up to now, in the art Bartonella infections are detected serologically under employment of an immunofluorescence assay. Therefor, for example monkey kidney epithelial cells are co-cultivated with Bartonella. Subsequently, microscopic slides are covered with the cell lysate that contains whole bacteria and cell debris. These slides were incubated with a serum of a patient. If such a serum contains antibodies against Bartonella, such antibodies will bind to the intact bacteria and could be visualized by means of a labeled secondary antibody (e.g. anti-human IgG) under fluorescence excitation. The manufacture of such antigen preparations and the performance of such immunofluorescence analyses are very costly, expensive and require special skilled staff and involve several potential sources of error. To the contrary, the before-explained method according to the invention can be easily handled, is reasonably practicable and produces correct results with a high liability.

Within the frame of this method, in the biological sample, e.g. in the blood serum, the presence of antibodies against the BadA protein or against fragments of this protein can be detected, i.e. by the usage of patient sera, for example within the frame of an immunoblot via the detection of specific antibodies in the serum, and it can be shown in an indirect way that in these patients an infection by Bartonella bacteria has been occurred in the past.

Another object of the present invention relates to a method for immunizing a cat against an infection by Bartonella henselae and/or BadA, comprising the steps: (a) providing a vaccinable solution containing Bartonella henselae and/or BadA, and (b) administering said solution to a cat.

The Bartonella henselae bacteria can be killed or genetically modified. Furthermore, the BadA protein can be altered or genetically modified as explained above in more detail. Step (b) can be repeated for several times until an activation of the immune system has taken place.

By this method it is ensured that cats as the main carrier of Bartonella henselae and causers of the cat scratch disease (CSD), will no longer be receptive for an infection by Bartonella henselae and, therefore, humans who are in contact with those cats are not endangered for becoming infected due to transmission of the bacterium from these cats.

It is to be understood that the features recited above and those yet to be explained below can be used not only in the respective combination indicated, but also in other combinations or in isolation, without departing from the scope of the present invention.

The present invention is now explained in more detail by means of embodiments, from which further advantages arise.

BRIEF DESCRIPTION OF THE DRAWINGS

FIG. 7A-D the nucleotide sequence SEQ ID No. 1 that is derived from BadA;

DESCRIPTION OF PREFERRED EMBODIMENTS

Example 1

Induction of a Genetic Program that Modifies the Angiogenesis by Bartonella henselae The inventors have infected HeLa cells with Bartonella henselae. 6 hours after the infection, these cells were compared to non-infected HeLa cells in a standard RNA microarray analysis (AFFYMETRIX MICROARRAY SUITE 5.0; AFFYMETRIX DATA MINING TOOL 3.0) in order to determine whether the infection results in an alteration of the genetic program of the cells. The infection itself was controlled by means of confocal laser scanning micros-copy. The result of such a microscopic analysis is shown in FIG. 1.

Figure 1:
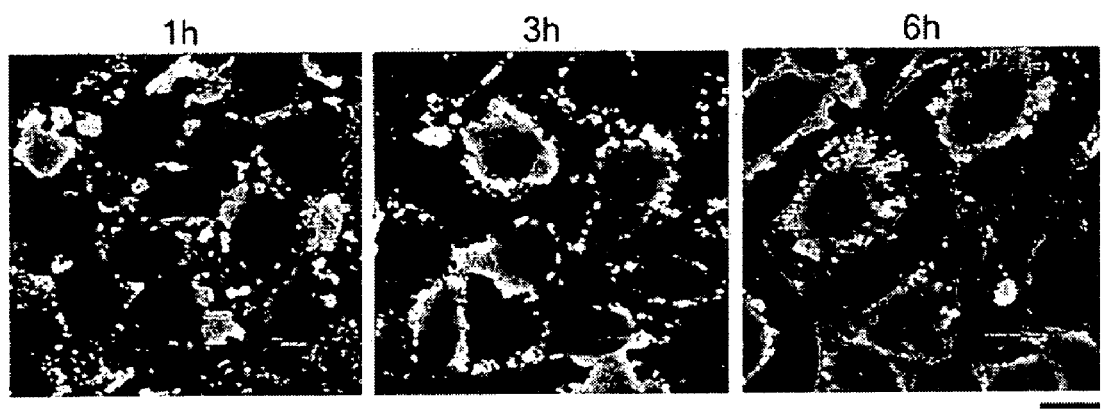
FIG. 1 the progress of an infection of HeLa cells by Bartonella henselae, analyzed by confocal laser scanning microscopy.

The left picture of the infected HeLa cells in FIG. 1 reflects the situation 1 hour, the picture in the middle 3 hours, and the right picture 6 hours after infection. The light structures which are located in the cytoplasm and which can be clearly seen in the central and the right picture correspond to bacteria which were detected by means of FITC-conjugated antibodies which were directed against the bacterium. The analysis of these pictures revealed that 6 hours after the infection>99% of the HeLa cells were infected.

The RNA microarray analysis showed that in the HeLa cells at least 7 genes were more than twofold up-regulated, which, as this has been described, are involved in the regulation of the angiogenesis and the vascularisation: Interleukin-8 (IL-8, 6,41-fold induction), Stanniocalcin-2 (STC2, 5,16-fold induction), Adrenomedullin (ADN, 3,88-fold induction), Ephrin A1 (EFNA1, 3,74-fold induction), Vascular Endothelial Growth Factor (VEGF, 3,54-fold induction), Insulin-like Growth Factor-Binding Protein-3 (IGFBP-3, 2,67-fold induction) and Endothelin 2 (ET-2, 2,13-fold induction). Except of IL-8 all of the analyzed induced genes are directly or indirectly regulated via the Hypoxia Inducible Factor-1 (HIF-1), the key transcription factor of the angiogenesis, suggesting that the main trigger for the induction of the genetic program by Bartonella henselae that modifies the angiogenesis, is HIF-1.

Figure 2:
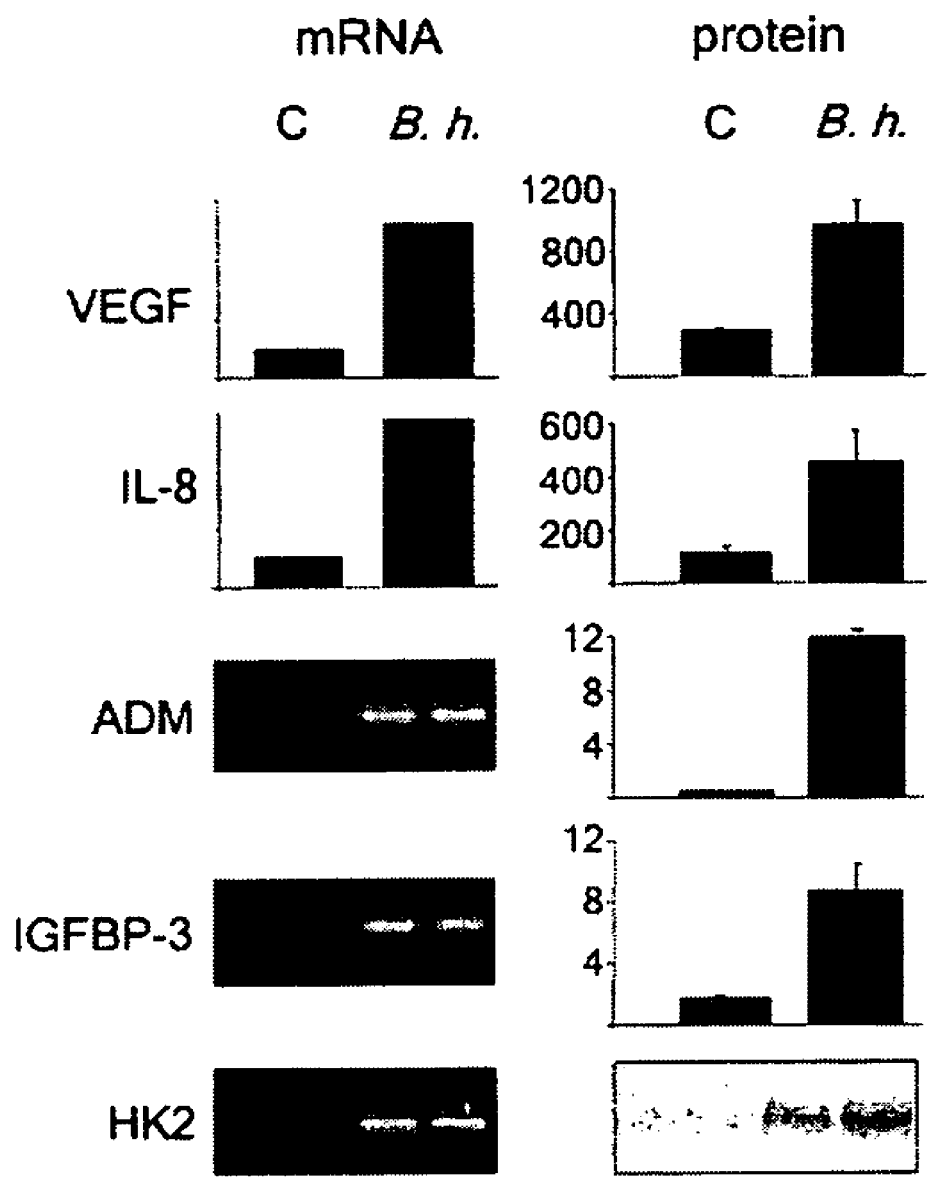
FIG. 2 the induction of proangiogenetic host cell transcripts and proteins in HeLa cells after an infection by Bartonella henselae.

The results which were obtained from RNA microarray analysis were verified by means of a quantitative real-time PCR or a semi-quantitative RT PCR, and on a protein level by means of Western blotting. The result of such an experiment is shown in FIG. 2.

For this, HeLa cells were infected by Bartonella henselae (B.h.), the total RNA was extracted 6 h after the infection and was transcribed into cDNA. The gene induction was evaluated by means of real-time PCR (VEGF, IL-8) or RT PCR (ADM, IGFBP-3, HK2). In order to determine the level of secreted protein, cells were infected and the supernatants of the cell cultures were analyzed 48 h after the infection by ELISA [VEGF (VEGF$_{165}$-ELISA-Kit, Quantikine, R & D Systems, Wiesbaden); IL-8 (Schulte et al. (2000), "*Yersinia enterocolitica* invasin protein triggers IL-8 production in epithelial cells via activation of Rel p65-p65 homodimers", *FASEB J* 14, 1471-1484)] or RIA [ADM (RKD10-10, Phoenix Pharmaceuticals, Karlsruhe, Germany); IGFBP-3 (Blum et al. (1990), "A specific radioimmunoassay for the growth hormone (GH)-dependent somatomedin-binding protein: its use for diagnosis of GH deficiency", *J Clin. Endocrinol. Metab* 70, 1292-1298)]. For Western blotting [HK2 (antibody SC6521, Santa Cruz)] 8 h after the infection cell extracts were prepared. C: Control, non-infected cells.

Also, these results verify the findings of the inventors, that an incubation of biological material, or an infection of HeLa cells with *Bartonella henselae* result in an induction of a genetic program that modifies angiogenesis. The level of mRNA and of protein of all angiogenesis-modulating factors which have been analyzed, were clearly increased after the infection.

Example 2

Activation of HIF-1 by *Bartonella henselae*

Figure 3:
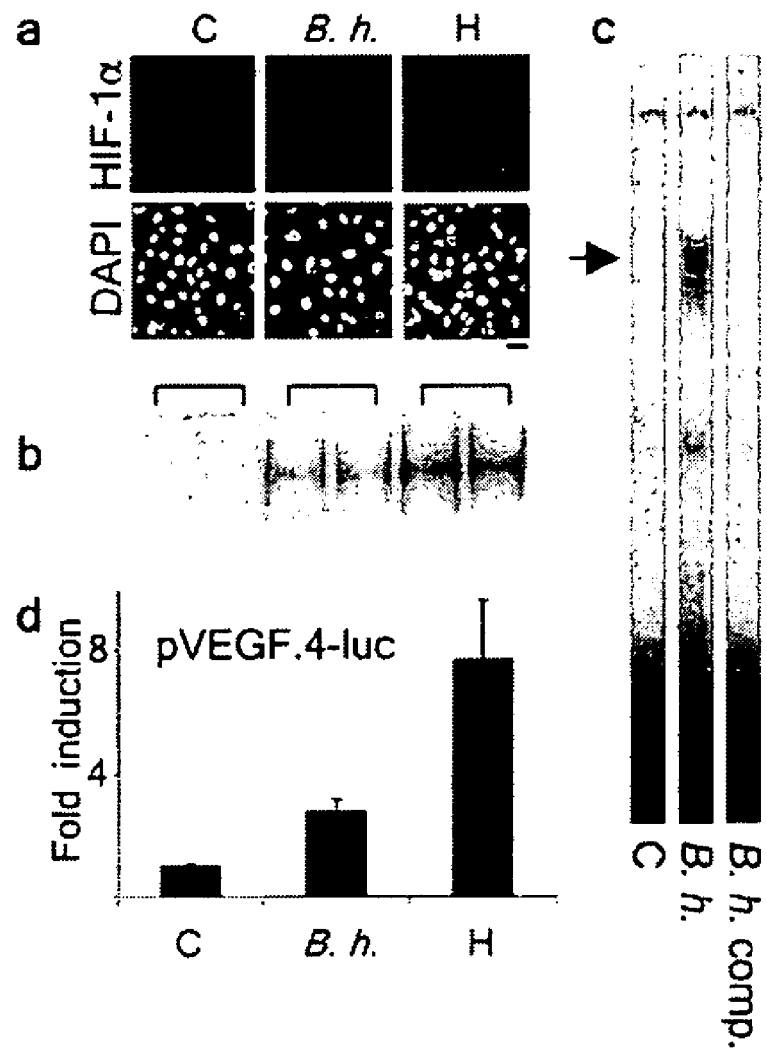
FIG. 3 the activation of HIF-1α in HeLa cells after an infection by Bartonella henselae.

In the following, the inventors have examined whether the transcription factor HIF-1 is also be induced in the host cell after an infection by *Bartonella henselae* has taken place. The results of corresponding experiments are shown in FIG. 3.

Picture (a) shows the detection of HIF-1 protein in HeLa cells 4 h after the infection by means of immunofluorescent staining under the usage of monoclonal antibodies which are specifically directed against HIF-1α (MB100- 131, Novus Biologicals, Littleton, Colo., USA) and TRITC-labeled secondary antibodies (Dianova, Hamburg, Germany), (upper row). The nuclei and bacteria were stained by DAPI (lower row). The depicted bar corresponds to 20 µm. It can be seen that 4 h after the infection with *Bartonella henselae* in the infected HeLa cells HIF-1α-associated signals appear in the nucleus (*B.h.*, central picture, light structures). This response can also be seen in hypoxia-treated cells (cf. Raleigh et al. (1998), *Cancer Res.* 58, 3765-3768), (H, right picture). In contrast, in non-infected HeLa cells virtually no HIF-1α can be detected (C, left picture).

The induction of HIF-1α protein in the HeLa cells was also verified by means of Western blots which were performed 4 h after the infection. The so obtained results (FIG. 3b) are consistent with those resulting from the immunofluorescence analysis. Here also a clear increase of the HIF-1α protein level can be observed in the HeLa cells 3 h after the infection by *Bartonella henselae*, whereas in non-infected control cells virtually no HIF-1α protein could be detected (cf. lanes 3-6 compared to 1 and 2).

The activation of HIF-1α was also verified by means of electromobility shift assays (EMSA) under usage of nucleic extracts (FIG. 3c). In competition experiments, nucleic extracts of *Bartonella henselae*-infected HeLa cells were incubated with a labeled HIF-1α probe in the presence of a 100-fold excess of non-labeled competitor probe (comp.). It follows that the transcription factor HIF-1 is in fact present in the nucleus and can bind to the corresponding target sequences of the host cell DNA.

In transfection experiments in which a VEGF promoter luziferase reporter was used, that is specifically regulated by HIF-1 (cf. Ikeda et al., (1995), *J Biol. Chem.* 270, 19761-19766) it turned out that the infection of HeLa cells by *Bartonella henselae* (*B.h.*) results in a VEGF gene transcription that is increased to a 3- to 4-fold level; by hypoxia (H) an 8- to 20-fold stimulation can be observed (FIG. 3d).

By the results which are shown in FIG. 3 arising from four independent methods it is demonstrated by the inventors, that by *Bartonella henselae* a modulation or activation of the angiogenesis occurs via an up-regulation of the HIF-1 transcription factor.

Example 3

Activation of HIF-1 in BA Biopsy Specimen

Figure 4:
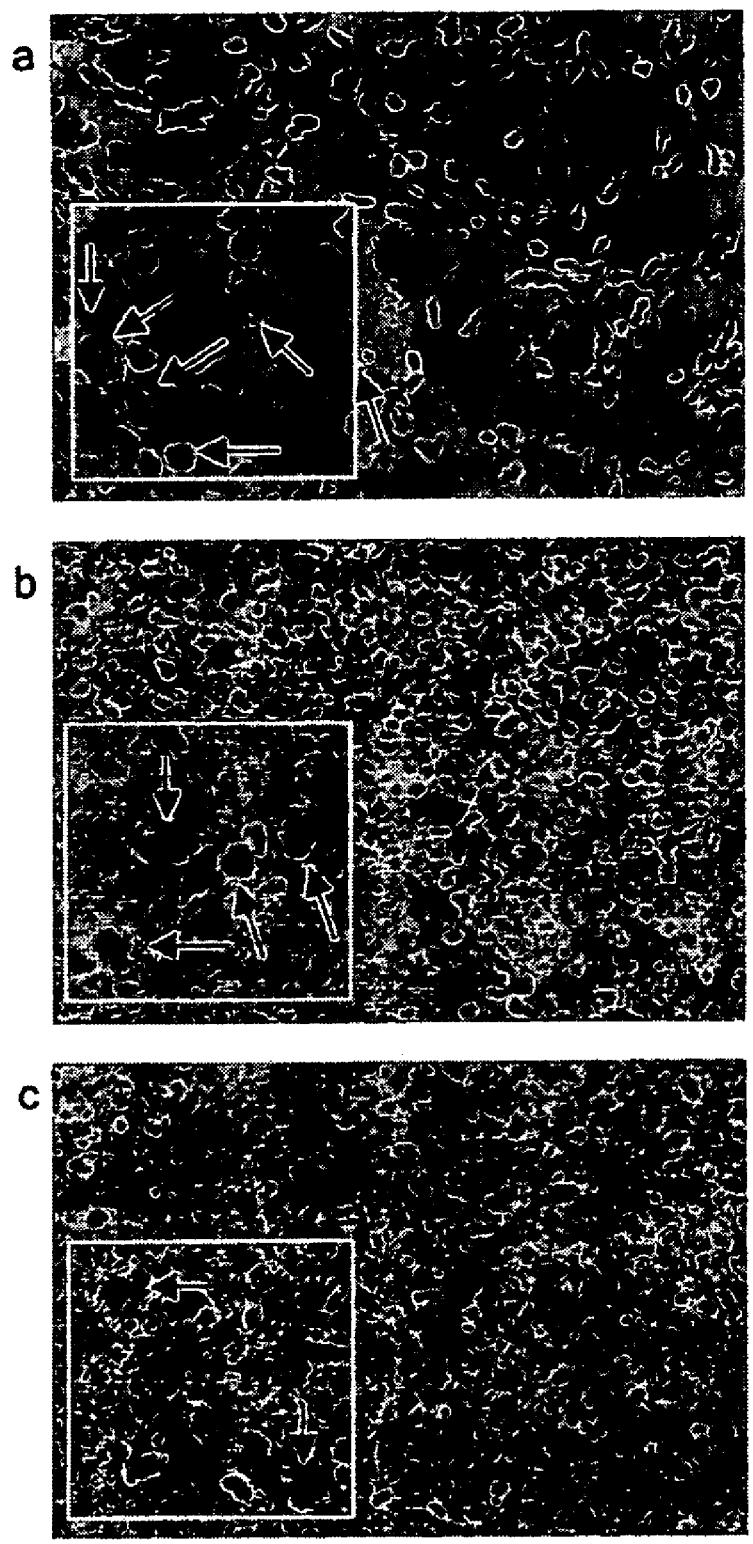
FIG. 4 the activation of HIF-1α in BA-patients' samples.

In order to analyze whether also in vivo in *Bartonella henselae*-infected tissues a HIF-1 activation occurs, sections of histological verified BA (bacillary angiomatosis) or BP (bacillary peliosis) lesions were examined for HIF-1α. The result of a corresponding experiment is shown in FIG. 4.

Picture (a) shows the analysis of the skin of a non-affected control person, and in pictures (b) and (c) the analysis of two histologically verified BA patients' samples are shown. For the detection of HIF-1α in the tissues a labeled antibody was used that is directed against HIF-1α (MB100-131, loc. cit.). It could be shown that in the patient samples (pictures (b), (c)) HIF-1α was very clearly present in the nuclei of histiocytes or macrophages which have infiltrated the BA lesions, whereas in the control tissue (picture (a)) the HIF-1α-associated signal is much weaker (see arrows).

These results prove that by an incubation or infection of biological material, such as for example HeLa cells, with *Bartonella henselae* a modulation of the angiogenesis via the induction of HIF-1 is not only possible in vitro, but also in vivo.

Example 4

*Bartonella henselae*-infected HeLa Cells are Viable

Figure 5:
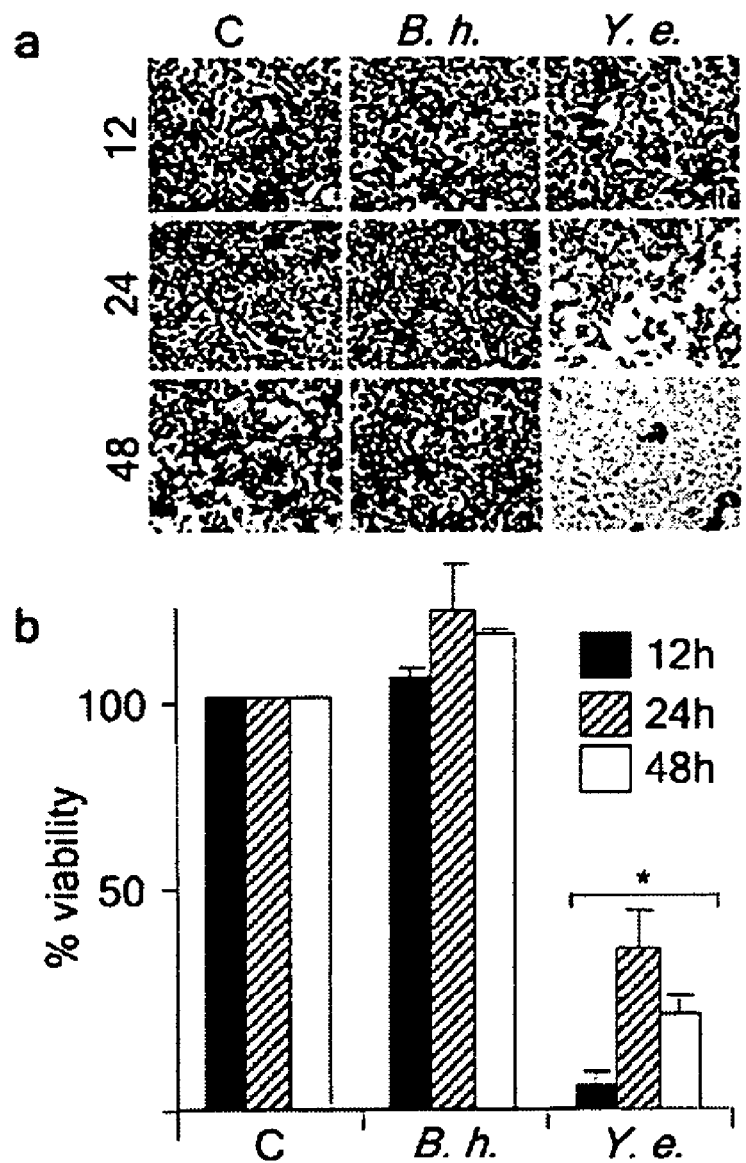
FIG. 5 the preservation of the viability of HeLa cells after an infection by Bartonella henselae.

HeLa cells were infected by *Bartonella henselae* and by *Y. enterocolitica* and the cellular morphology and the cellular viability was evaluated 12, 24 and 48 h after the infection. The result of such an experiment is shown in FIG. 5.

Picture (a) shows the evaluation of a Giemsa staining and picture (b) the evaluation of a MTS assay (CELLTITER-96 AQ$_{NEOUS}$; Promega, Mannheim, Germany). The viability of non-infected control cells (C) was set to 100%. Each calculated value corre-sponds to the average out of three samples of each group. * indicates a significant difference compared to the control ($p<0.05$).

It arises from this experiment that the infection of the HeLa cells by *Bartonella henselae* (*B.h.*) up to 45 h after the infection does not result in a decrease of the cellular viability (cf. FIG. 3a, central column; FIG. 3b, central lanes). To the contrary, the cellular viability was dramatically decreased after an infection by *Y. enterocoliticia* (*Y.e.*) (cf. FIG. 3a, right column, FIG. 3b, right lanes).

This experiment indicates the pharmacological tolerance or suitability of *Bartonella henselae* and its therapeutical potential as an active agent of a pharmaceutical composition.

Example 5

Induction of an Angiogenesis-modifying Genetic Program by the Adhesin A Protein of *Bartonella henselae* (BadA)

Figure 6:
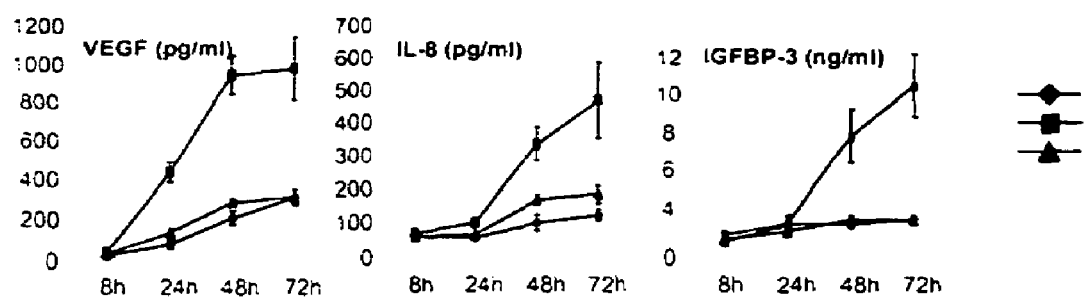
FIG. 6 the induction of proangiogenetic factors in HeLa cells after an infection by Bartonella henselae depending on BadA.

Since the before-shown experiments demonstrate that the incubation or infection of biological material, such as HeLa cells or tissues, by *Bartonella henselae* results in an up-regulation of angiogenesis-modifying genes, which are controlled by the key transcription factor of the angiogenesis HIF- 1, it was also analyzed by the inventors, whether a specific bacterial protein can be found that is responsible for this biological effect. In connection with this it was also tested, whether the surface protein of *Bartonella henselae*, BadA, having a molecular weight of 340 kD and that has been detected by the inventors, is involved in the modulation of the angiogenesis or the up-regulation of angiogenesis-modulating host cell components, such as the Vascular Endothelial Growth Factor (VEGF), Interleukin-8 (IL-8), Insulin-like Growth Factor Binding Protein-3 (IGFBP-3). In these experiments two mutants of *Bartonella henselae* were used, which do not express the BadA protein (BadK mutants), as well as wild type *Bartonella henselae* as a control. With these *Bartonella henselae* bacteria HeLa cells were infected and cultivated, the cell culture supernatants were removed 8, 24, 48 and 72 h after the infection, centrifuged and frozen at −20° C. The VEGF concentration in the supernatants was determined by the usage of a human $VEGF_{165}$ ELISA Kit (cit. loc.), IL-8 was determined by means of ELISA, as described in Schulte et al. (cit. loc.). The IGFBP-3 that was secreted into the cell culture supernatant was measured under the usage of a specific RIA, cf. concerning this Blum et al. (cit. loc). The result of such an experiment is shown in FIG. 6.

This experiment shows that an infection of HeLa cells by the two BadA⁻ mutants (-♦- first mutant; -▲- second mutant) does not result in any increase of the production of angiogenesis-modulating factors, whereas the infection by wild type *Bartonella henselae* (-■-) causes a clear increase of angiogenesis-modulating cytokines in the correspondingly infected HeLa cells.

In further experiments the BadA- mutants were complemented by the introduction of an expression vector that expresses functional BadA protein, i.e. the mutants were subsequently again in the condition to synthesize BadA and to insert it into the membrane. While performing the before-mentioned experiment, it could be demonstrated that such complemented BadA- mutants are again in the condition to stimulate the production of angiogenesis-modulating factors, such as VEGF (data not shown).

It follows that BadA is a crucial bacteria factor of *Bartonella henselae* that is responsible for modulating the angiogenesis and, therewith, is suitable as an active agent in a pharmaceutical composition for the modulation of the angiogenesis.

The DNA nucleotide sequence encoding the bacterial BadA protein is indicated as SEQ ID No. 1 and shown in FIG. 7. As usual, the presentation starts with the 5'-end that comprises the initiation codon (ATG), and extends to the 3'-end that comprises the stop codon (TAA). The last 111 nucleotides at the 3'-end encode the so-called membrane anchor domain that is responsible for insertion of the protein into the bacterial membrane.

Example 6

BadA as the Key Factor in the Adhesion of *Bartonella henselae* to Endothelial Cells After that, the inventors have analyzed whether BadA is involved in the adhesion of *Bartonella henselae* to endothelial cells, among other things in order to get information about the possible mode of action of the modulation of the angiogenesis.

Figure 8:
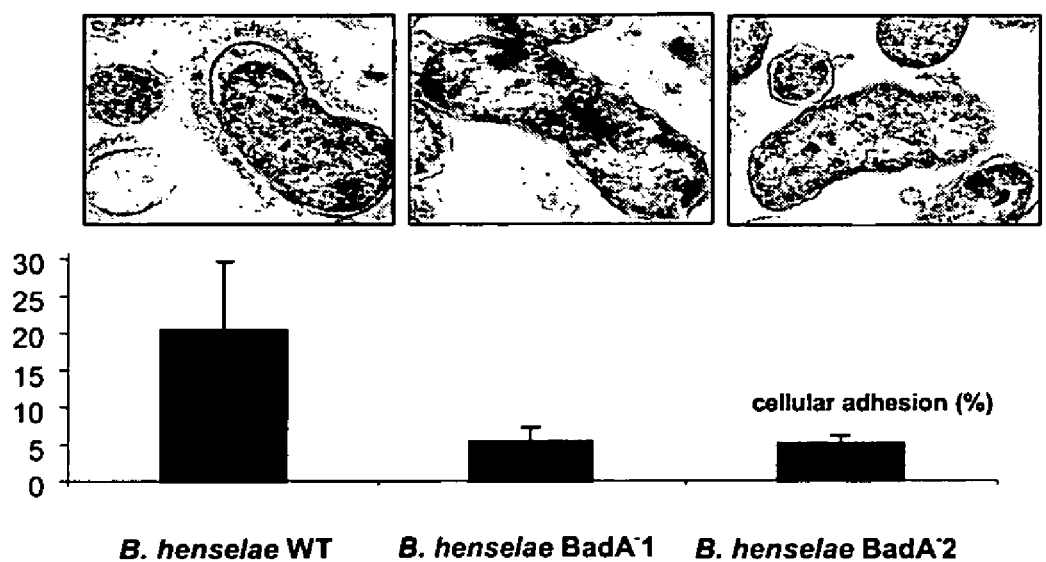
FIG. 8 the adhesion of Bartonella henselae depending on BadA.

For this, endothelial cells were infected by the before-mentioned *Bartonella henselae* bacteria (wild type, two different BadA⁻ mutants) and 30 min after the infection the amount of adhering bacteria was determined. For doing this, the cell culture supernatants were carefully removed, the cells were thoroughly washed with Clicks (RPMI 1640 medium), lysed and the total amount of adhering bacteria was determined. The results of such an experiment are shown in FIG. 8.

In the upper illustrations as a control it is demonstrated by transmission electron microscope that wild type *Bartonella henselae* expresses, as expected, BadA on its surface (see arrows, left picture), whereas the two BadA⁻ mutants do not express any BadA (central and right picture).

Furthermore, it is shown by this experiment that a BadA⁻ mutation results in a dramatical decrease of the adhesion of the corresponding mutant to endothelial cells (lower picture; compare central and right column to left column).

The before-described observations concerning the adhesion of the wild type or genetically modified *Bartonella henselae* bacteria, were also verified by means of immunofluorescence analysis via laser scanning microscopy staining (data not shown).

In further experiments, the BadA⁻ mutants were complemented by the introduction of an expression vector that expresses functional BadA protein (cf. example 5). While performing these before-explained experiments it turned out that such complemented BadA⁻ mutants are again in the position to adhere to endothelial cells. It could also be demonstrated that BadA⁻ mutants, in contrast to *Bartonella henselae* wild type bacteria, were no more able to bind to fibronectin and collagen. This loss was recovered by the introduction of the above-mentioned BadA encoding expression vector into the mutants (data not shown).

These results indicate that the modulation of the angiogenesis by *Bartonella henselae* is mediated by the adhesion of BadA to the biological material, for example to the endothelial cells.

Example 7

BadA as a Diagnostic Marker for Infections by *Bartonella*

In another experiment the inventors have analyzed whether antibodies directed against BadA can be found in human sera of patients who are affected by an infection with *Bartonella henselae*, or of rabbits and mice infected with viable or heat-killed *Bartonella henselae*.

Figure 9:
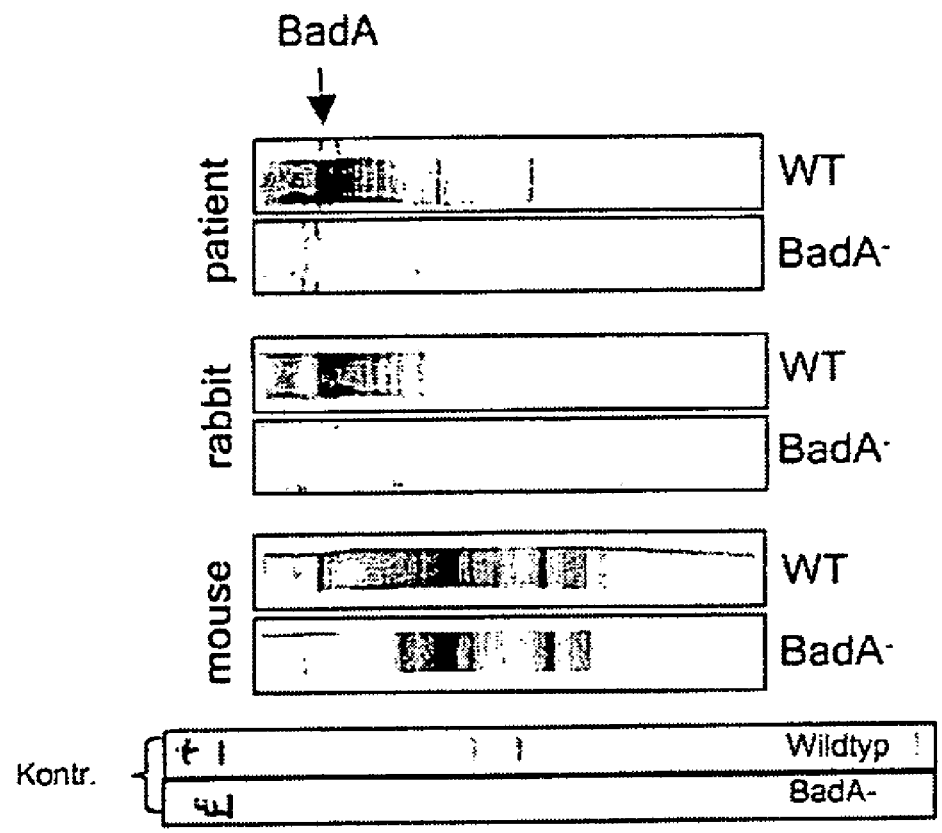
FIG. 9 the immunoreactivity of sera of CSD patients, a rabbit infected with viable Bartonella henselae, and a mouse immunized with heat-killed Bartonella henselae, for BadA.

For this wild type bacteria of *Bartonella henselae* and BadA⁻ mutants of *Bartonella henselae* were separated by electrophoresis and transferred onto a blotting membrane. The membrane was incubated with human sera which came from patients suffering from cat scratch disease (CSD), or from healthy control patients, or from infected rabbits and mice. The result of such an experiment is depicted in FIG. 9.

In the respective upper lanes wild type bacteria lysate (WT) was separated, whereas in the respective lower lanes BadA⁻ bacteria lysate (BadA⁻) was separated, blotted and afterwards incubated with sera of CSD patients, sera of rabbits infected by viable *Bartonella henselae*, or sera of mice infected by heat-killed *Bartonella henselae*. In the lowest two lanes, wild type and BadA⁻ bacteria lysate were separated and incubated with serum of a healthy control person.

The arrow indicates the position of the separated BadA. It can be seen that by means of the sera that came from a CSD-affected patient (patient), or infected mice or rabbits, BadA protein is detected, consequently their immune systems have produced antibodies against the BadA protein, whereas in the human serum that came from the healthy control person (Kontr.) no antibodies against BadA are contained and therefore no immunoreactive band on the level of the BadA protein appears. Since the BadA⁻ mutants do not comprise any BadA protein no immunoreactive band on the level of the BadA protein can be found.

In total, seven out of eleven sera coming from CSD patients showed a reactivity against BadA, compared to one out of nine sera coming from healthy control persons.

These experiments demonstrate that BadA is a suitable diagnostic marker for identifying *Bartonella* infections.

What is claimed is:

1. A pharmaceutical composition for the stimulation of angiogenesis, comprising an isolated adhesin A protein of the *Bartonella henselae* bacterium (BadA) and a pharmaceutically acceptable carrier.

2. The pharmaceutical composition according to claims 1, wherein BadA protein is encoded by a nucleic acid comprising SEQ ID No. 1.

3. A method for treating an human or animal being in need of stimulation of angiogenesis, comprising administering the pharmaceutical composition of claim 1.

4. The method according to claim 3, wherein the stimulation is performed during treatment of an ischaemic disease.

5. The method according to claim 3, wherein the stimulation is performed during treatment of a tumor disease.

* * * * *

UNITED STATES PATENT AND TRADEMARK OFFICE
CERTIFICATE OF CORRECTION

PATENT NO. : 7,638,489 B2  Page 1 of 1
APPLICATION NO. : 11/429657
DATED : December 29, 2009
INVENTOR(S) : Kempf et al.

It is certified that error appears in the above-identified patent and that said Letters Patent is hereby corrected as shown below:

At page 1 (Item 56), column 2, line 7, please delete "Prinicples" and insert therefore, -- Principles --.

At page 2 (Item 56), column 1, line 4, please delete "microascular" and insert therefore, -- microvascular --.

At page 2 (Item 56), column 1, line 6, please delete "trasposon" and insert therefore, -- transposon --.

At column 2, line 18, please delete "potentional" and insert therefore, -- potential --.

At column 5, line 10, please delete "Therefor," and insert therefore, -- Therefore, --.

At column 7, line 64, please delete "luziferase" and insert therefore, -- luciferase --.

At column 8, line 46, please delete "corre-sponds" and insert therefore, -- corresponds --.

At column 9, line 15, please delete "(BadK" and insert therefore, -- (BadA⁻ --.

At column 19, line 21, please delete "claims," and insert therefore, -- claims --.

At column 19, line 21, after "wherein" please add -- the --.

At column 20, line 15, please delete "an" and insert therefore, -- a --.

At column 20, line 15, please delete "being".

Signed and Sealed this

Eighth Day of June, 2010

David J. Kappos
*Director of the United States Patent and Trademark Office*

UNITED STATES PATENT AND TRADEMARK OFFICE
CERTIFICATE OF CORRECTION

PATENT NO. : 7,638,489 B2  Page 1 of 1
APPLICATION NO. : 11/429657
DATED : December 29, 2009
INVENTOR(S) : Kempf et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 525 days.

Signed and Sealed this

Twenty-first Day of December, 2010

David J. Kappos
*Director of the United States Patent and Trademark Office*

```
                        SEQUENCE LISTING

<160> NUMBER OF SEQ ID NOS: 1

<210> SEQ ID NO 1
<211> LENGTH: 9156
<212> TYPE: DNA
<213> ORGANISM: Bartonella henselae

<400> SEQUENCE: 1
atgttttgga tgtgctttgt aatttttttc attggagaat ttattatgaa aaaattatct      60
gtcacatcaa agagacaata taatttatat gcttcgccta tttctcgacg tttatctttg     120
ttaatgaagc tctcattgga aactgtaaca gttatgttct tattgggtgc atctcctgta     180
ttggcttcga atcttgcgct tacaggagca aagaatctga gtcaaaactc tccaggtgta     240
aattactcta aaggtagcca tggtagtatt gttctctctg gtgatgatga tttttgcggt     300
gcggattatg ttcttggtcg tggaggcaat tctactgtac gtaatgggat tccaataagt     360
gtagaagaag aatatgagag atttgtcaaa caaaaattaa tgaataatgc tacttctcct     420
tatagtcaga gttcagagca acaagtttgg actggtgatg ggctaacaag caaaggttcg     480
ggttatatgg gagggaagtc gactgacggt gataaaaata tcttgcctga ggcttatggt     540
atatattctt ttgcaactgg ttgtggttct tctgcgcagg ggaattattc agttgcattt     600
ggtgcaaatg caactgcact tactgggggg tcgcaagctt ttggtgttgc tgcacttgca     660
agtggaaggg taagtgttgc tattggtgta gggtcagaag cgacgggaga ggctggagtt     720
tctttgggtg gactctcaaa ggcagctggt gctcgtagtg ttgctatagg gacgcgggcc     780
aacgcttacg gtgaagaatc tattgcgata ggtggtggct taaaacaggg cagtgataat     840
aagatcggtt cagctgtagc gcagggtctg aaagcgattt ctataggttc tgattctgtt     900
ggttttcagc actatgcagt tgctattggt gctaaatccc gtgctcttct cttgaaaagt     960
gttgccttgg gttcttattc tgttgctgat gttgatgctg gcgttagagg ttatgatcct    1020
gtggaggatg agccatcgaa aaacgttagt tttgtatgga aaagctctgt aggtgctgtt    1080
agtgttggta atcgtaaaga aggcttaacg cgacaaatta taggagttgc agctggtact    1140
gaagacactg atgcagtaaa tgttgcacag ctaaaagcat taggggaat gatatcagaa    1200 aaaggaggtt ggaatcttac tgttaataat gacaataata cagttgttag ttcaggtggt    1260
gcattagatt tgtcatctgg aagtaaaaat ctcaaaattg caaagatgg aaaaaagaat    1320 aatgtaacct ttgatgtcgc tagggatctc acgttaaaga gcataaaatt agacggtgtt    1380
actttaaatg aaacaggttt atttattgca aacggaccac aaatcaccgc ttcaggtatt    1440
aatgctggta gtcaaaaaat tacaggcgta gcagagggta ctgatgcgaa cgatgcagta    1500
aactttggac aactgaagaa aattgaaaca gaagtcaaag aacaagtagc agccagtggc    1560
tttgtgaaac aggatagcga tacaaaatac cttaccattg gtaaggatac agatggcgat    1620
acaatcaata ttgctaataa caaaagtgat aagcgtactc tcatgggcat aaaggagggt    1680
gacatctcaa aagactcgag tgaagctatc accggttcac agctatttac tacaaatcaa    1740
```

-continued

```
aatgtgaaaa ctgtatcaga taatctccaa acagcagcca cgaatatagc taagactttt      1800
ggaggtgatg ccaaatatga agatggtgaa tggactgctc cgacatttaa agttaaaact      1860
gttaccggtg aaggcaagga agaagagaag acgtatcaga atgtagcgga tgccttggct      1920
ggagttggaa gttccatcac caatgttcag aataaagtga ctgaacaagt taataatgcg      1980
attactaaag tggaaggcga tgccttatta tggagcgatg aagctaatgc ctttgtggcg      2040
cgtcatgaaa agagtaagtt agaaaaaggc gcatctaaag cgacacaaga aaacagcaag      2100
attacgtatc tgttagatgg tgatgtttcg aaagattcca cggatgctat tacaggtaaa      2160
cagctttatt cattaggtga taagattgca tcttatttag gtggtaacgc taaatatgag      2220
aatggtgaat ggactgcacc tacctttaag gttaaaacag ttaaggaaga tggtaaggaa      2280
gaagagcaga cgtatcataa tgtagcagcg gcttttgaag gagttggtac gtctttcacg      2340
aatgtgaaaa atgaaattac taaacagatt aatcatctcc agtctgatga ttcagcggtt      2400
gttcattatg ataaagatga taaaaacggc agtattaatt atgcgagtgt aaccttgggt      2460
aaaggtaaag attctgcagc tgttacccct cataatgtcg ctgcaggtaa tattgctaag      2520
gattcacatg atgcaatcaa tggtagccaa atttattctc tgaacgagca acttgcgacc      2580
tattttggtg gcggtgctgg ttataataag gaaggcaaat ggactgctcc aacttttaca      2640
gtcaagacag ttaaggaaga tggtgaggaa gaagagaaga cgtatcagaa tgtagcggaa      2700
gctttgactg gagttggtac gtctttcacc aatataaaaa gtgagattac taaacagatt      2760
gctaatgaga ttagcaatgt aacaggtgat agtcttgtta agaaagatct cgatacgaat      2820
cttatcacca ttggtaaaga agtagcaggt actgaaatca atatagcaag cgtttctaaa      2880
gctgaccgga ctctttctgg tgttaaggaa gcagtaaaag ataatgaagc tgttaacaaa      2940
gggcagcttg ataaaggttt gaagcatctt tctgacagtc tccagtccga agattcagca      3000
gttgttcatt atgataaaaa gacagatgaa actggtggca ttaattatac gagcgtgacg      3060
ttgggaggta agataagac ccctgttgcc cttcataatg tcgctgatgg tagtatttcc      3120
aaggattcac atgatgccat caatggcgga cagattcata caatcggtga ggatgttgca      3180
aaattcttgg gtggagcagc aagctttaac aacggtgctt ttaccggccc aacttataag      3240
ttgtcgaata ttgatgcaaa gggtgatgta caacagagtg agtttaaaga tataggttca      3300
gcctttgcgg gtcttgatac gaacatcaag aatgtcaata ataatgtaac gaataagttt      3360
aatgaactta ctcaaaacat aacgaatgtt acgcaacagg taaaaggcga tgccttatta      3420
tggagcgatg aagccaatgc ctttgtggcg cgtcatgaaa agagcaagtt aggaaaaggt      3480
gcatctaaag cgacacaaga aaacagcaag attacgtatc tgttagatgg tgatgtttcg      3540
aaagattcca cggatgctat tacaggtaaa cagctttatt cattaggtga taagattgca      3600
tcttatttag gtggtaacgc taaatatgag atggtgaat ggactgcacc tacctttaag      3660
gttaaaacag ttaaggaaga tggtaaggaa gaagagaaga cttatcagaa tgtagcggaa      3720
gctttgactg gagttggtac gtctttcacg aatgtgaaaa atgaaattac taaacagatt      3780
aatcatctcc agtctgatga ttcagcggtt gttcattatg ataagaataa agatgaaact      3840
ggtggcatta attatgcgag tgtaaccttg ggtaaaggta agattctgc agctgttacc      3900 cttcataatg ttgctgatgg tagtatttcc aaggattcac gtgatgccat caatggtagc      3960
caaatttatt ctctgaacga gcaacttgcg acctattttg gcggcggtgc taagtacgag      4020
aatggccaat ggaccgctcc tattttaaa gtcaagacag ttaaggaaga tggtgaggaa      4080
```

```
gaagagaaga cgtatcagaa tgtagcggaa gctttgactg gagttggtac gtctttcaca   4140
aatataaaga gtgagattac taaacagatt gctaatgaga ttagcagtgt aacaggtgat   4200
agtcttgtta agaaagatct cgccacgaat cttatcacca ttggtaaaga agtagcaggt   4260
actgaaatca atatagcaag cgtttctaaa gctgaccgga ctctttctgg tgttaaggaa   4320
gcagtaaaag ataatgaagc tgttaacaaa gggcagcttg ataccaatat caagaaagta   4380
gaagataaat taacagaagc agtcggtaaa gttacgcaac aggtgaaagg tgatgcttta   4440
ttgtggagca atgaagataa cgcgtttgtt gctgatcatg gtaaggatag tgcaaagaca   4500
aagagcaaga ttacacattt attagatgga aatattgcgt ctggctcaac cgatgccgtt   4560
accggtggtc aactctattc tctgaacgag caacttgcga cctattttgg cggcggtgct   4620
aagtacgaga atggccaatg gactgcacct acctttaagg ttaaaacagt taacggtgaa   4680
ggcaaggaag aagagcagac ttatcagaat gtagcggaag ctttgactgg agttggtgcg   4740
tctttcatga atgttcagaa taaaattact aatgaaatta ccaatcaagt taataacgca   4800
attacgaaag tagaaggcga tagtcttgtg aagcaagata tcttggtat tattacgctt   4860 ggtaaagaaa gaggtggttt gaaagttgat tttgcaaatc gtgatggttt agatcggact   4920
ctttctggtg taaggaagc ggtaaacgat aatgaagcag ttaataaagg ccagcttgat   4980
gccgatatca gtaaagttaa taataatgta acgaataagt ttaatgaact tactcaaaac   5040
ataacgaatg ttacgcaaca ggtaaaaggc gatgccttat tatggagcga tgaagctaat   5100
gcctttgtgg cgcgtcatga aaagagtaag ttagaaaaag gcgtatctaa agcgacacaa   5160
gaaaatagca agattacgta tctgttagat ggtgatattt cgaaaggttc cacggatgcc   5220
gttaccggtg gtcagcttta ttctctgaac gagcaacttg cgacctattt tggtggcgat   5280
gctaagtacg agaatggcca atggactgca cctaccttta aggttaaaac agttaacggt   5340
gaaggcaagg aagaagagca gacgtatcat aatgtagcag cagcttttga aggagttggt   5400
acgtctttca ccaatataaa aagtgagatt actaaacaga ttaataatga gattagcaat   5460
gtaaaaggtg atagtcttgt taagaaagat ctcgccacga atcttatcac cattggtaaa   5520
gaagtagcgg gtactgaaat caatatagca agcgtttcta aagctgaccg gactctttct   5580
ggtgtaaagg aagcagtaaa agataatgaa gctgttaaca aagggcagct tgataccaat   5640
atcaagaaag tagaagataa attaacagaa gcagtcggta agttacgca acaggtaaaa   5700 ggtgatgctt tattgtggag caatgaagat aacgcgtttg ttgctgatca tggtaaggat   5760
agcgcaaaga caaagagcaa gattacacat ttattagatg gaaatattgc gtctggctca   5820
accgatgccg ttaccggtgg tcagctttat tctctgaacg agcaacttgc gacctatttt   5880
ggcggcggtg ctaagtacga gaatggccaa tggactgcac ctacctttaa ggttaaaaca   5940
gttaacggag atggcaagga agaagagcag acttatcaga atgtagcgga agctttgact   6000
ggagttggta cgtctttcac gaatgttcag aataaaatta ctaatgaaat taccaatcaa   6060
gttaataacg caattacgaa agtagaaggc gatagtcttg tgaagcaaga taatcttggt   6120
attattacgc ttggtaaaga aagaggtggt ttgaaagttg attttgcaaa tcgtgatggt   6180
ttagatcgga ctctttctgg tgtaaaggaa gcggtaaacg ataatgaagc agttaataaa   6240
ggccagcttg atgccaatat cagtaaagtt aataataatg taacgaataa gtttaatgaa   6300
cttactcaaa acataacgaa tgttacacaa caagttcaag gtgatacttt attatggagc   6360
gatgaagcta atgcctttgt ggcgcgtcat gaaaagagta agttagaaaa aggcgtatct   6420
aaagcgacac aagaaaatag caagattacg tatctgttag atggtgatat ttcgaaaggt   6480
```

-continued

| | |
|---|---|
| tccacggatg ccgttaccgg tggtcagctt tattctctga acgagcaact tgcgacctat | 6540 |
| tttggcggcg gtgctaagta cgagaatggt gaatggaccg cacctacctt taaggttaaa | 6600 |
| acagttaacg gtgaaggcaa ggaagaagag cagacgtatc ataatgtagc agcagctttt | 6660 |
| gaaggagttg gtacgtcttt caccaatata aaaagtgaga ttactaaaca gattgataat | 6720 |
| gagattatca atgtaaaagg tgatagtctt gttaagagag atctcgctac gaatctcatc | 6780 |
| accattggta agaaatagaa aggcagtgca atcaatattg ctaataagag tggtgaagct | 6840 |
| cggaccattt ctggtgtaaa ggaagcagta acaataatg aagctgttaa caaagggcaa | 6900 |
| cttgatacca atatcaagaa agtagaagat aaattaacag aagcagtcgg taaagttacg | 6960 |
| caacaggtaa aaggtgatgc tttattgtgg agcaatgaag ataacgcgtt tgttgctgat | 7020 |
| catggtaagg atagcgcaaa gacaaagagt aagattacac atttattaga tggaaatatt | 7080 |
| gcgtctggct caaccgatgc cgttaccggt ggtcaactct attctcttaa cgagcaactt | 7140 |
| gcgacctatt ttggcggcgg tgctaagtac gagaatggcc aatggactgc acctagcttt | 7200 |
| aaggttaaaa cagttaagga agatggcaag gaagaagagc agacgtatca gaatgtagcg | 7260 |
| gaagctttga ctggagttgg tacgtctttc acgaatgtga aaaatgaaat tactaaacag | 7320 |
| attaatcatc tccagtctga tgattcagcg gttgttcatt atgataagaa taaagatgaa | 7380 |
| actggtacca ttaattatgc gagtgtaacc ttgggtaaag gtaaagattc tgcagctgtt | 7440 |
| acccttcata atgtcgccga tggtagtatt tccaaggatt cacgtgatgc catcaatggt | 7500 |
| ggacagattc atacaatcgg tgaggatgtt gcaaaattct gggtggaga tgcagctttt | 7560 |
| aaagatggtg cttttaccgg cccaacttat aagttgtcga atattgatgc aaagggtgat | 7620 |
| gtacaacaga gtgagtttaa agatataggt tcagcctttg cgggtcttga tacgaacatc | 7680 |
| aagaatgtca ataataatgt aacgaataag tttaatgaac ttactcaaag cataacgaat | 7740 |
| gttacgcaac aggtaaaagg cgattcctta ttatggagcg atgaagccaa tgcctttgtg | 7800 |
| gcgcgtcatg aaaagagcaa gttagaaaaa ggtgcatcta agcgataca agaaaatagc | 7860 |
| aagattacgt atctgttaga tggtaatgtt tcgaaaggtt ccacggatgc cgttactggt | 7920 |
| ggtcagcttt attcaatgag caacatgctt gcgacctatt taggtggtaa cgctaaatat | 7980 |
| gagaatggtg aatggaccgc acctaccttt aaggttaaaa cagttaacgg tgaaggcaag | 8040 |
| gaagaagagc aaacttatca gaatgtagcg gaagctttga ctggagttgg tacgtctttc | 8100 |
| accaatataa aaagtgagat tgccaaacag attaatcatc tccagtctga tgattcagcg | 8160 |
| gttattcatt atgataagaa taaagatgaa actggcacca ttaattatgc gagtgtaact | 8220 |
| ttgggtaaag gtgaagattc tgcagctgtt gcccttcata atgtcgctgc aggtaatatt | 8280 |
| gctaaggatt cacgtgatgc aatcaatggt tctcagcttt attctttgaa cgagcagtta | 8340 |
| ttgacctatt ttggcggtaa tgctggctat aaagatgggc aatggatagc tcccaaattc | 8400 |
| caagtttcgc agttcaagag tgatggtagt tctggtgaga aggagagcta tgataatgta | 8460 |
| gcggctgcgt ttgaaggagt taacaaaagt cttgcaggta tgaacgagcg tattaataat | 8520 |
| gttgttactg ctggccagaa tgtttcgtcg aacagtttaa attggaatga cacagaggga | 8580 |
| ggttatgacg ctcgtcataa tggtgtggac agtaagctca cgcatgtaga gaatggtgac | 8640 |
| gtatccgaaa aatcgaaaga agccgttaat ggaagtcaac tatggaatac gaatgagaaa | 8700 |
| gttgaagcgg ttgagaagga tgtaaagaat attgagaaga aggtacaaga tattgctaca | 8760 |
| gtagcagata gtgctgttaa gtatgagaaa gatagtactg gcaagaaaac gaatgtaatc | 8820 |

```
-continued aaattagttg gtgggagtga aagtgatcca gtattgatag acaatgtagc ggatggtgac    8880
attaaagaag gctctaagca ggcagtcaat ggaggtcagt tgcgtgatta tactgagaaa    8940
cagatgaaga tagtgcttga agatgcgaag aaatatacgg atgaacgctt caatgatgtc    9000
gtcaataatg gtgttaatga ggctaaagct tatacagata tgaagtttga ggctttaagt    9060
tacgctgttg aggatgtccg taaagaagca agacaggcgc agctattggt ttggcggtat    9120
ctaacttacg ttactatgat ataccgggat ctttaa                              9156
```